US006767350B1

(12) United States Patent
Lob

(10) Patent No.: US 6,767,350 B1
(45) Date of Patent: Jul. 27, 2004

(54) FIXING ELEMENT FOR BONE FRAGMENTS

(76) Inventor: Helke Lob, Ehrwalderstrasse 82, D-81377, Munich (DE)

( * ) Notice: Subject to any disclaimer, the term of this patent is extended or adjusted under 35 U.S.C. 154(b) by 0 days.

(21) Appl. No.: 09/744,514

(22) PCT Filed: Jul. 20, 1999

(86) PCT No.: PCT/EP99/05194

§ 371 (c)(1), (2), (4) Date: Apr. 2, 2001

(87) PCT Pub. No.: WO00/06037

PCT Pub. Date: Feb. 10, 2000

(30) Foreign Application Priority Data

Jul. 25, 1998 (DE) .......................................... 198 35 096

(51) Int. Cl.⁷ .............................................. A61B 17/68
(52) U.S. Cl. .............................. 606/63; 606/72; 606/73; 606/74
(58) Field of Search .............................. 606/72, 73, 60, 606/63, 66, 68, 74, 75; 623/17.11, 17.15, 17.16; 411/15, 21, 24, 25, 32–34, 38

(56) References Cited

U.S. PATENT DOCUMENTS

| | | | | |
|---|---|---|---|---|
| 2,381,050 A | * | 8/1945 | Hardinge | 606/65 |
| 2,490,364 A | * | 12/1949 | Livingston | 606/68 |
| 4,790,304 A | | 12/1988 | Rosenberg | |
| 5,004,421 A | * | 4/1991 | Lazarof | 433/173 |
| 5,268,001 A | * | 12/1993 | Nicholson et al. | 606/72 |
| 5,437,674 A | | 8/1995 | Worcel | |
| 5,470,230 A | * | 11/1995 | Daftary et al. | 433/174 |
| 5,480,403 A | * | 1/1996 | Lee et al. | 606/72 |
| 5,489,210 A | * | 2/1996 | Hanosh | 433/173 |
| 5,713,904 A | | 2/1998 | Errico | |
| 5,782,918 A | * | 7/1998 | Klardie et al. | 606/60 |
| 5,980,522 A | * | 11/1999 | Koros et al. | 606/61 |
| 6,142,782 A | * | 11/2000 | Lazarof | 433/174 |
| 6,168,597 B1 | * | 1/2001 | Biedermann et al. | 606/73 |
| 6,227,860 B1 | * | 5/2001 | Hobo | 433/173 |
| 6,287,310 B1 | * | 9/2001 | Fox | 606/63 |
| 6,443,989 B1 | * | 9/2002 | Jackson | 623/17.15 |
| 6,506,051 B2 | * | 1/2003 | Levisman | 433/173 |

FOREIGN PATENT DOCUMENTS

| | | |
|---|---|---|
| CA | 2205407 A1 | 6/1996 |
| DE | 44 44 510 A1 | 6/1996 |
| EP | 0 409 364 A2 | 1/1991 |

* cited by examiner

*Primary Examiner*—Kathryn Ferko
*Assistant Examiner*—Kathryn Odland
(74) *Attorney, Agent, or Firm*—Hahn Loeser & Parks, LLP; Robert J. Clark

(57) ABSTRACT

The invention relates to a fixing element for fixing a first bone fragment (5.1), notably an ankle-bone fragment in ankle joint fractures, to a corresponding second bone fragment (5.2). Said element comprises an elongated spreading part (2) and a fixing part (1) which can be introduced into aligned holes (4, 6) in the bone fragments (5.1, 5.2). The fixing part has a proximal first section (1.1) designed to be introduced into the first bone fragment (5.1) and an adjoining distal second section (1.2) designed to be introduced into the second bone fragment (5.2), as well as a hollow cavity (3) extending substantially along its full length. The fixing part (1) is configured such that it can be fully introduced into the holes (4, 6); by proximal introduction of the spreading part (2) into the hollow cavity (3) at right angles to its longitudinal direction can be spread open by wedge action at least in the area of its two ends so as to be joined to the corresponding bone fragment (5.1, 5.2); and after introduction of the spreading part (2) has a greater transverse dimension at the distal end of the second section (1.2) than at the proximal end of said section.

23 Claims, 5 Drawing Sheets

FIXING ELEMENT FOR BONE FRAGMENTS

Figure 1:
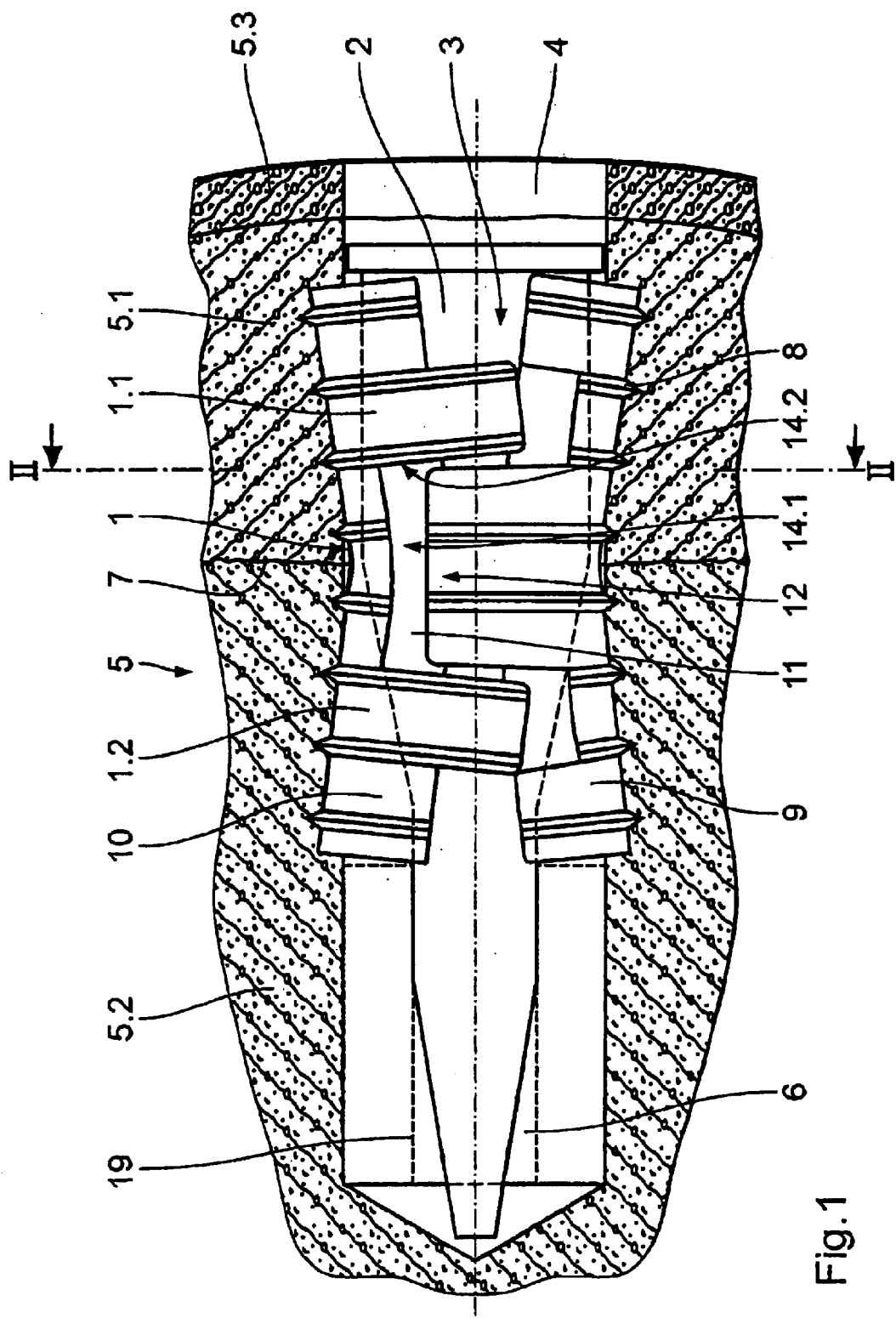

The invention concerns a fixing element for fixing a first bone fragment to a corresponding second bone fragment, as in an ankle joint fracture.

A problem which frequently arises in the case of fractures caused by over-stressing is that relatively small exposed bone regions are detached from the rest of the bone. Thus for example ankle fractures represent the most frequent break injury to the lower extremity. In that case, over-stressing in the region of the upper ankle joint means that the Inner ankle Is detached from the tibia and/or the outer ankle is detached from the fibula. In order to restore the function of the ankle joint, the ankle fragments must be fixed to the associated bone fragment until the break heals. Bone screws and the like are still frequently used for that purpose. As however generally particularly long and/or a plurality of bone screws are required for adequate stabilisation of the bone fragments by virtue of the slenderness of the bone screws, the fixing elements of the general kind set forth which are easier and quicker to implant are increasingly gaining in importance.

European patent application EP 0 409 364 A2 discloses a fixing element of the general kind set forth, in which at its proximal end, that is to say the end towards the surgeon, the fixing body has a step which permits the fixing body to be inserted into the receiving bores in the bone fragments, only as far as a given depth. The fixing body which in the initial condition has a conical main body with anchoring elements arranged thereon is spread open in particular at its distal end, by driving in the spreading body, to such an extent that the main body assumes a substantially cylindrical contour. The anchoring elements of the spread-open regions in that case penetrate into the surrounding bone and thus serve to provide for additional fixing.

That fixing element however suffers from the disadvantage that the presence of the step at the proximal end means that It Is only suitable for fixing bone fragments up to a given maximum dimension in the longitudinal direction of the fixing body. If that maximum dimension is exceeded, there is no longer any guarantee that the first bone fragment is adequately fixed to the second bone fragment. As the distal end of the fixing body is spread open In the spongiosa which is generally of low strength, it can tear out of the second bone fragment with a correspondingly short depth of penetration or in a situation involving locally reduced strength of the bone tissue. It is precisely a locally reduced level of strength in the bone tissue that can only be detected with difficulty during the operation, so that, with a depth of penetration which is possibly still sufficient in a normal situation, it can nonetheless tear out.

If the step at the proximal end of the fixing body is omitted, the fixing body can admittedly penetrate sufficiently far into the second bone fragment, irrespective of the dimension of the first bone fragment. As the spreading body at the proximal end is of a smaller diameter than the cavity, no expansion of the fixing body takes place immediately at the proximal end. Rather, expansion of the fixing body increases slowly in the direction towards the distal end so that the absence of the step means that there is precisely no guarantee of secure fixing of relatively thin first bone fragments.

The known fixing element in its respective configurations is therefore only limitedly suitable for fixing bone fragments of the most widely varying dimensions so that in practice an expensive set of fixing elements in a plurality of different dimensions is required for the respective situations of use.

U.S. Pat. No. 5,713,904 B1 to Errico, et al. (Feb. 3, 1998), discloses a fixing element of the general kind set forth, in which an integral tubular fixing body is provided at both ends with longitudinal slots so that, upon the insertion of a suitable spreading body into its internal cavity, it is spread open in a cup-shaped configuration at both ends while it remains undeformed in its central region. The fixing body in that case is provided with a male screwthread by which of which it can be screwed into the bore in the bone.

That fixing element has the disadvantage however that, in its middle region, the contact force between the fixing body and the surrounding bone is determined by the fit therebetween. In that respect, it is precisely in the comparatively soft spongiosa of a bone that a greater or lesser deviation of the bore diameter from its target diameter can occur, due to a minor deflection with the drill from the target axis for the bore. Depending on the over-size of the bore with respect to the fixing body, the situation can then involve a connection which is movable to a correspondingly greater or lesser degree transversely with respect to the longitudinal direction of the fixing body, if the central region of the fixing body is precisely in the region of the join between two bone fragments which are to be fixed to each other.

Therefore the object of the present invention is to provide a fixing element of the general kind set forth, which does not suffer from the above-stated disadvantages or which suffers therefrom at least to a lesser degree, and which in particular can be put to flexible use and ensures reliable fixing.

Based on a fixing element as set forth in the appending claims, that object is attained by the features recited therein.

The invention involves the technical teaching that a fixing element which can be put to flexible use is acquired if the fixing body is adapted to be introduced completely into the bores and by proximal insertion of the spreading body into the cavity can be spread open transversely with respect to its longitudinal direction by a wedge action substantially over its entire length for connection to the respective bone fragment. That ensures on the one hand that, irrespective of the thickness of the first bone fragment, the fixing body can be moved into a position in which the second portion of the fixing body is sufficiently deeply inserted into the second bone fragment in order to ensure fixing of the first bone fragment, which is adequate in any situation. In that respect, spreading the fixing body open in the region of its proximal end ensures that, even when dealing with particularly thin first bone fragments, reliable fixing is guaranteed with the fixing element according to the invention.

Reliable fixing is further achieved in that, in the spread condition, that is to say after substantially complete insertion of the spreading body into the cavity, the fixing body at the distal end of the second portion is of a larger dimension transversely with respect to its longitudinal direction than at the proximal end of the second portion. The fixing body is thus enlarged conically or bell-like at its distal end in the second bone fragment in which it is generally surrounded by spongiosa of lower strength, thereby achieving a positively locking engagement over a large area. That ensures secure anchoring even if the surrounding bone material is of a possibly reduced level of strength, insofar as it applies the anchoring loads uniformly to a larger volume of bone. That effectively prevents the fixing body from being torn out of the second bone fragment.

The operative surfaces in the region of the cavity and on the spreading element, which are responsible for spreading open the fixing body, can be designed in many known ways. Thus to provide that the second portion of the fixing body is expanded in a conical or bell-like manner, it is only necessary for the transverse dimension of the cavity to decrease towards the distal end. In that respect, the transverse dimension of the spreading element can remain constant or also decrease towards the distal end, in which case the decrease per unit of length must then be less than the decrease in the transverse dimension of the cavity towards the distal end.

The fixing body can consist of a single body which, for greater ease of being spread open in the regions which are to be spread apart, is provided with a respective one or preferably a plurality of longitudinal slots or the like. If the fixing body has a plurality of those longitudinal slots, the spreading action which varies in the peripheral direction additionally provides for non-rotationally securing the fixing body about the longitudinal axis thereof. Preferably, the fixing body comprises at least two body portions which are in adjoining relationship In the peripheral direction and which are connected together movably sufficiently for being spread open. In that respect, the connection only has to be so firm that, upon being introduced into the bores and upon Introduction of the spreading element into the cavity, the body portions are held relative to each other in the longitudinal and peripheral directions, at least until the spreading element and the wall of the bore take over that function in the spreading procedure. In this case, the spreading effect which varies in the peripheral direction additionally provides for non-rotationally securing the fixing element about the longitudinal axis thereof.

The body portions can be connected by way of suitably thin leg-like bridging regions which are connected to the body portions and which, when the fixing element Is spread open, are correspondingly slightly stretched, unfolded or torn open. It is however also possible to provide on each of the body portions respective guide elements which co-operate with the corresponding guide elements of the adjoining body portion and which thus hold the body portions relative to each other in the longitudinal and peripheral directions. Thus for example projections with one or more substantially tangentially extending guide surfaces on one body portion can co-operate with guide grooves of a corresponding configuration on the adjoining body portion.

In preferred embodiments of the invention, the operative surfaces of the fixing body and the spreading body, which co-operate to spread the fixing body open, are of such a configuration that spreading of the second portion begins at the distal end of the second portion. That ensures that a distribution of stress which is as uniform as possible is achieved in the spreading operation in the second portion and thus local stress peaks are substantially avoided both in the fixing body and also in the bone.

The operative surfaces In the region of the cavity and on the spreading element, which are responsible for spreading open the fixing body, can be designed for that purpose in many known ways. Thus, for conical or bell-like expansion of the second portion of the fixing body, which begins at the distal end, it is only necessary for the transverse dimensions of the cavity and the spreading body to decrease towards the distal end, in which case the transverse dimension of the cavity and of the spreading body substantially correspond to each other at the distal end and the reduction in the transverse dimension of the spreading body per unit of length must be less than the reduction in the transverse dimension of the cavity towards the distal end.

In that respect, it is particularly advantageous if the operative surfaces are such that at least a first part of the first portion is spread open before the second portion is spread open. In that way, the reduction in the size of the second portion, as a consequence of its conical or bell-shaped spreading beginning at the distal end, is transmitted by way of the first part, which is already spread open, of the first portion, to the first bone fragment, so that the latter is pressed against the second bone fragment in a manner which is advantageous in terms of the healing process. In that respect, it is further preferable for the first part to be arranged in the region of the proximal end of the first portion, so that this advantage can also be enjoyed in the case of a thin first bone fragment.

In particularly advantageous developments of the fixing element according to the invention the first portion is pivotably connected at its distal end by way of at least one web or leg element to the proximal end of the second portion. In that case, the fixing body and the spreading body are of such a configuration that, upon insertion of the spreading body, the distal end of the first portion is substantially completely spread open before in succession in a first step a part of the second portion is spread open and in a second step the proximal end of the second portion is spread open. Alternatively, the fixing body and the spreading body can be of such a configuration that upon insertion of the spreading body the proximal end of the second portion is substantially completely spread open before in succession in a first step a part of the first portion is spread open and in a second step the distal end of the first portion is spread open. In addition, the configuration and arrangement of the leg element is such that the longitudinal spacing between the first and second portions is reduced during the second step.

That provides in a simple manner that the reduction in the longitudinal spacing between the first and second portions is transmitted to the first and second bone fragments, by way of the regions of the first and second portions respectively which are already connected to the respective bone fragment by virtue of being spread open when the reduction in length is initiated. In that way, the bone fragments are not only firmly fixed relative to each other but they are also pressed against each other in a manner which is advantageous in terms of the healing process.

In that respect, the leg element or elements can be simply arranged on the two portions in such a way that their angle of inclination relative to the longitudinal axis of the fixing body increases during the second step, thereby directly affording a corresponding reduction in the longitudinal spacing between the first and second portions.

In advantageous variants of the invention the fixing body, after insertion of the spreading body into the cavity, is of a larger dimension transversely with respect to its longitudinal direction at the proximal end of the first portion than at the distal end of the first portion. The conical or bell-shaped expansion achieved In that way at the proximal end of the fixing body promotes the careful application of load to the bone tissue of the bone fragment in question, in the manner which has already been described hereinbefore in respect of the distal end.

The fixing element according to the invention is distinguished in that the fixing body is adapted to spread open substantially over the entire length thereof. That ensures an appropriately distributed application of load to the bone tissue, which is adapted to the strength conditions thereof.

In particularly advantageous variants of the fixing element according to the invention the first portion in the non-spread condition is of a larger dimension transversely with respect to its longitudinal direction than the second portion. In that case, optimum positioning of the fixing body is guaranteed in a simple and reliable manner insofar as the second bone fragment is bored in the preparatory operation with a correspondingly smaller diameter than the first bone fragment. The resulting step in the region of the fracture gap then forms an abutment for the fixing body which accordingly, without further aids, can be introduced into the second bone fragment to the optimum depth of penetration, irrespective of the thickness of the first bone fragment.

The fixing element according to the invention preferably has for optimum fixing in the bone tissue at the surface of the fixing body which is towards the bone, projections which are intended to penetrate into the bone. The projections can be designed in many known ways. For example, they can be of a tooth-like or pin-like or spike-like or other configuration both In the longitudinal direction and alternatively or additionally in the peripheral direction, in order to provide for barb-like hooking engagement into the bone tissue. In that case they can be arranged to extend around the fixing body at the periphery thereof for example in rings or in a screwthread-like configuration.

It will be appreciated that the components of the fixing element according to the invention comprise biocompatible materials. Particularly advantageous variants of the fixing element according to the Invention provide that at least the fixing body comprises a bioresorbable material so that there is no need for subsequent explantation. It will be appreciated that preferably all components of the fixing element are made up of such bioresorbable materials in order entirely to avoid subsequent explantation of individual components. It will be appreciated that this can also be rendered unnecessary by virtue of using materials with long-term biocompatibility, for example for the spreading body. All biocompatible or bioresorbable materials with a level of time-dependent creep strength which is adequate for fixing can be used as the materials, the fixing body preferably comprising a polylactide. That is further preferably reinforced in regions involving an increased tensile loading by tension-resistant, in particular bioresorbable fibers and/or fiber cloth. In that case, it is possible to use for example tension-resistant materials as are used for surgical suture materials. An example in that respect is bioresorbable polyglactide.

Figure 2:
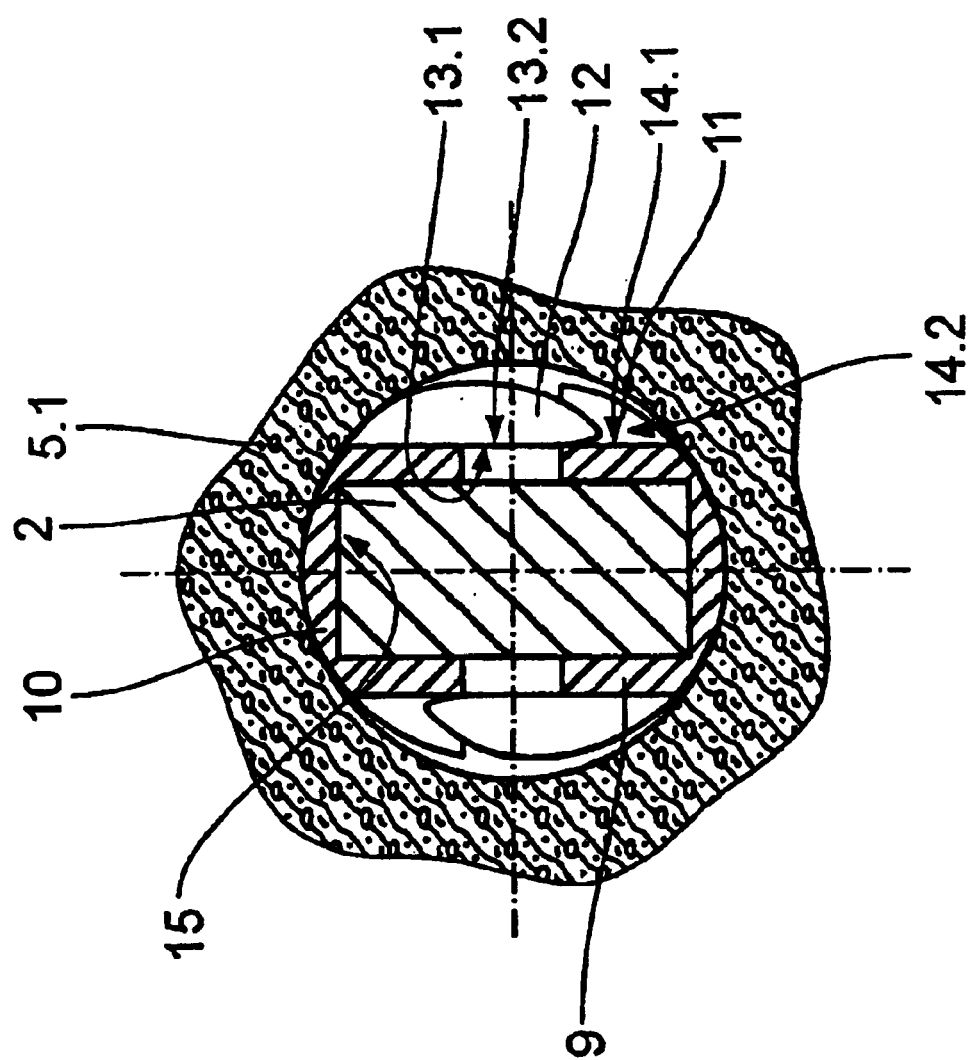
Figure 3:
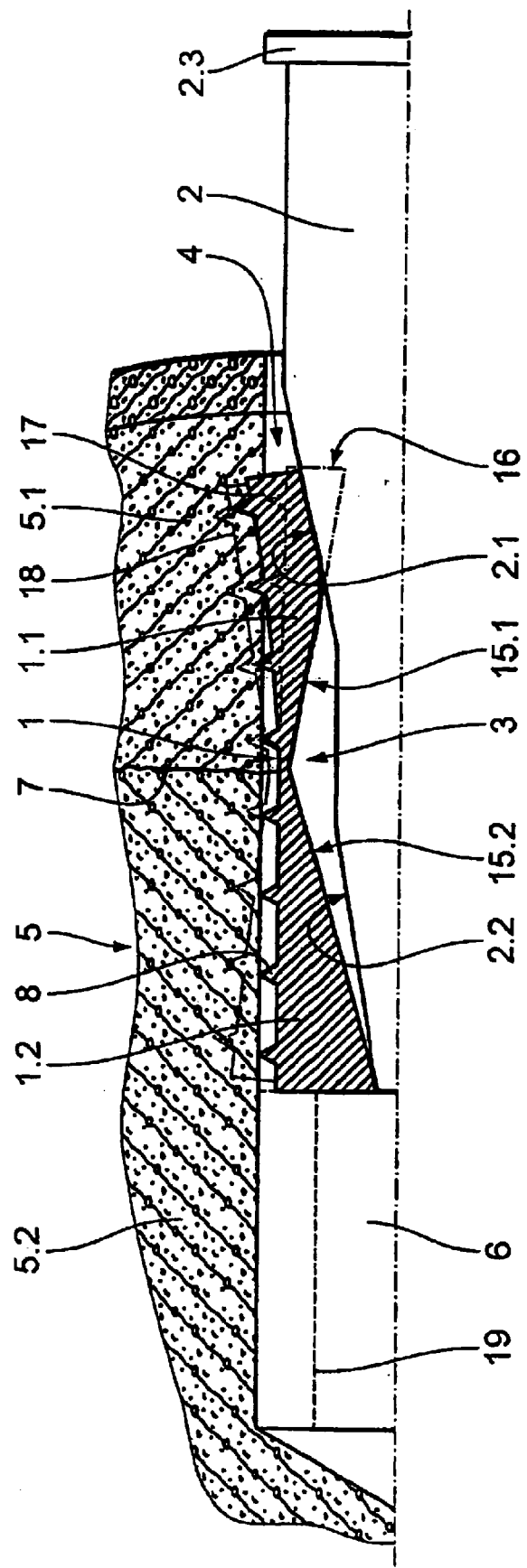
Figure 4:
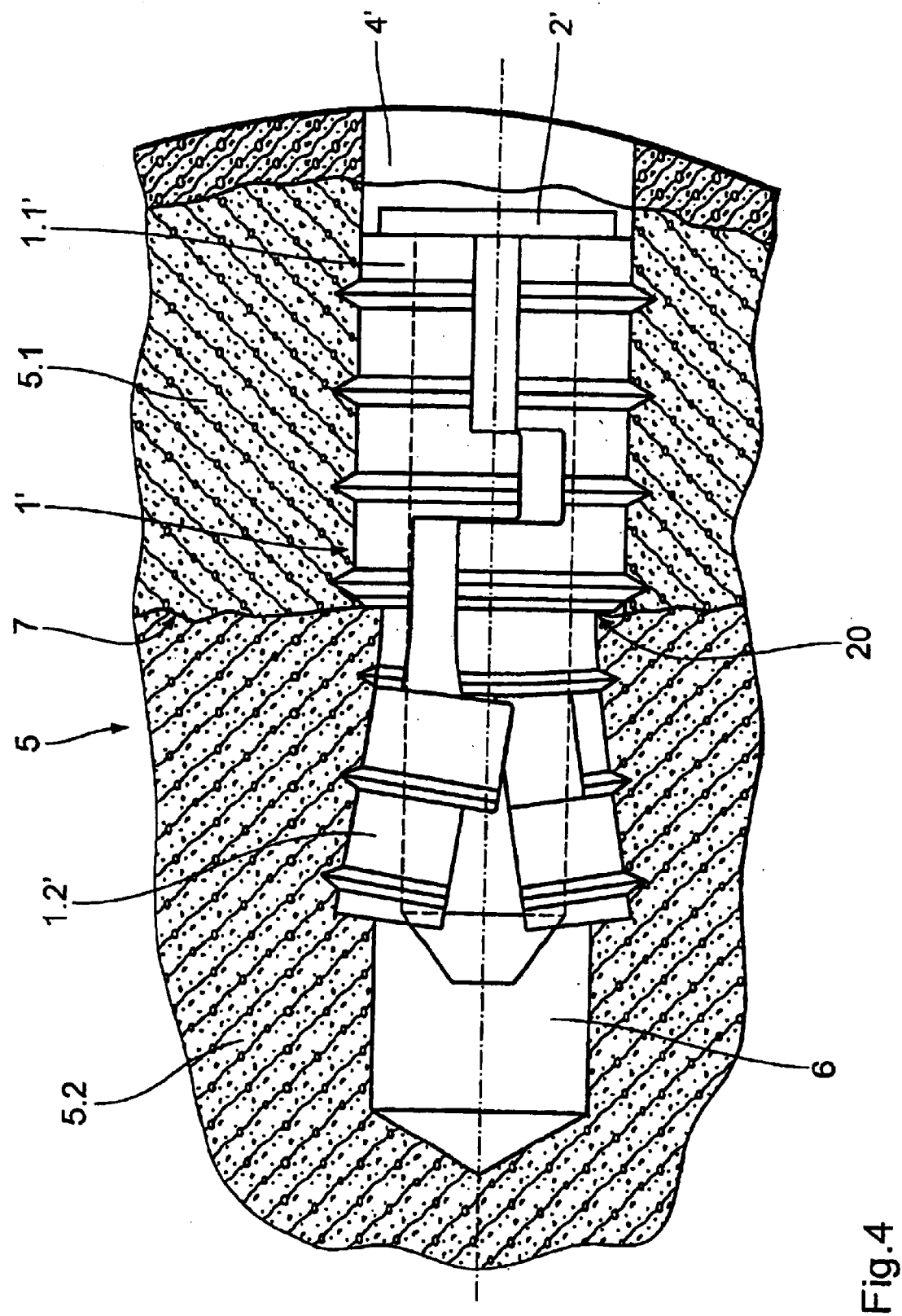
Figure 5:
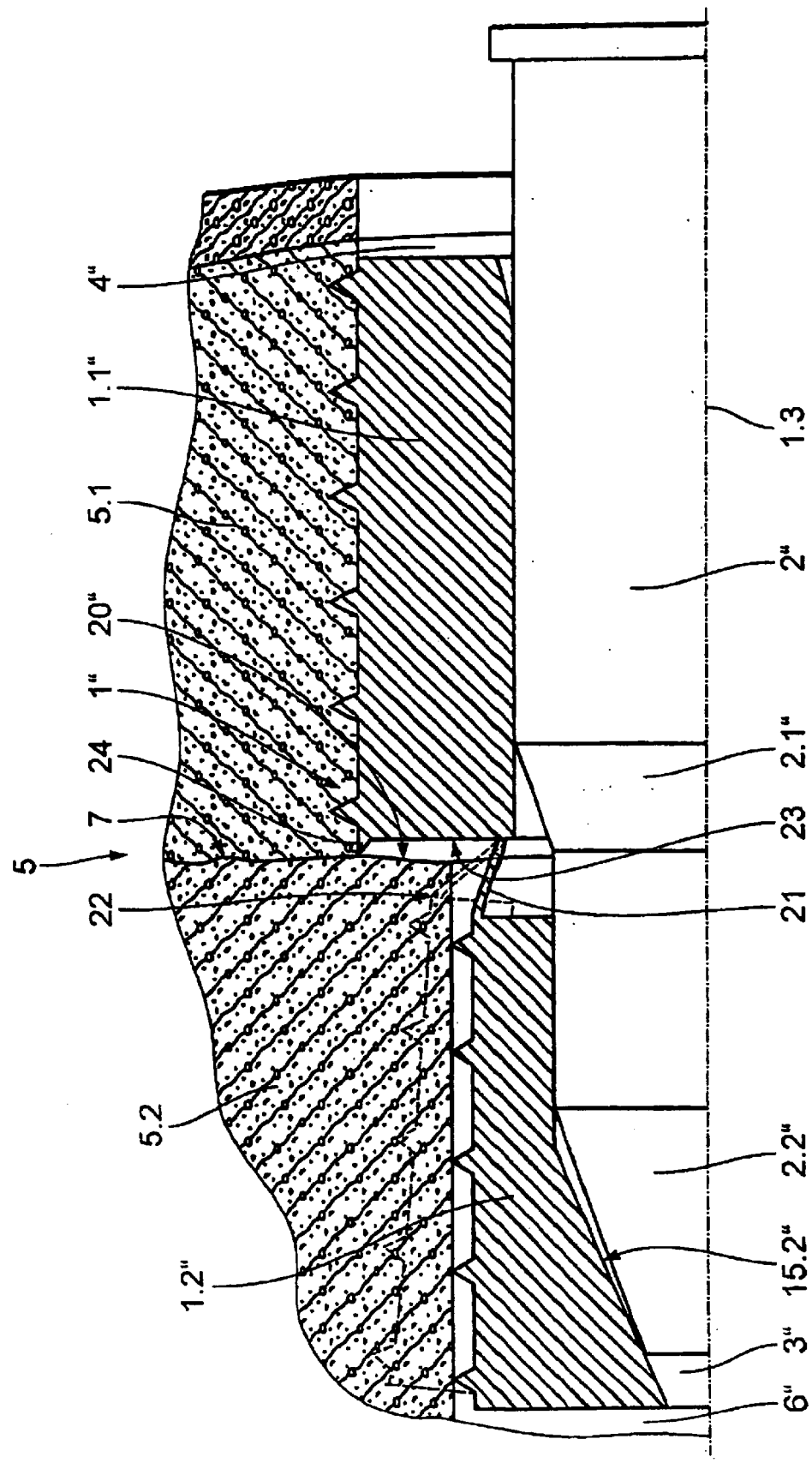

Other advantageous developments of the invention are characterised in the appendant claims or described in greater detail hereinafter together with the description of preferred embodiments of the invention with reference to the drawings in which:

FIG. 1 shows a preferred embodiment of the fixing element according to the invention in the spread condition, FIG. 2 is a view in section taken along line II—II in FIG. 1, FIG. 3 is an axial section through the embodiment of FIG. 1 in the partially spread condition, FIG. 4 shows a further embodiment of the fixing element according to the invention in the spread condition, and FIG. 5 shows an axial section through another embodiment of the fixing element according to the invention In the partially spread condition.

FIG. 1 shows an embodiment of the fixing element according to the invention comprising an elongate fixing body 1 and a spreading body 2 which was introduced into the cavity 3 extending over the entire length of the fixing body 1. The fixing body 1 is fitted with its proximal first portion 1.1 in a bore 4 in the first fragment 5.1 of the bone 5 and with Its distal second portion 1.2 in the bore 6, which is aligned with the bore 4, in the second fragment 5.2 of the bone 5. In the illustrated example the bone 5 is the tibia in the region of the upper ankle joint, from which the first bone fragment 5.1 was detached in the region of the inner ankle as a result of a fracture 7.

In order to fix the first bone fragment 1.1 to the second bone fragment 1.2, the fixing body was firstly introduced into the repositioned bone fragments 1.1 and 1.2 completely to the illustrated depth into the bores 4 and 6 and then spread by a wedge action over its entire length by introduction of the spreading body 2 into the cavity 3, whereby parts of the fixing body penetrate into the surrounding bone 5. That provides for a fixed connection to the two bone fragments 5.1 and 5.2 and thus fixing of the bone fragments 5.1 and 5.2 relative to each other.

The spreading body 2 and the cavity 3 in the fixing body 1 are so matched to each other that the fixing body 1 is spread open at the distal end of the second portion 1.2 further than at the proximal end of the second portion. In the region of the bore 6 the second bone fragment 5.2 comprises spongy bone tissue which is of relatively low local strength. The wider spreading-open effect at the distal end of the second portion 1.2 than at the proximal end produces a positively locking connection between the bones 5, with a relatively large contact area. That large contact area ensures that the fixing loads which are applied distributed over the contact surface to the surrounding bone do not result in local stresses in the bone, which exceed the local strength of the bone and which can thus result in loosening of the connection to such an extent that the fixing element tears or breaks out. That affords a particularly good and reliable hold for the fixing element in the second bone fragment 5.2.

In the illustrated example the proximal end of the first portion 1.1 is also spread open further than its distal end. That involves also using the above-described effect of uniform application of load to the bone 5, when connecting the fixing element to the first bone fragment 1.1. That is particularly advantageous when the first bone fragment is a fragment whose thickness, as in the illustrated example, markedly exceeds the length of the first portion of the fixing body and therefore the first portion of the fixing body is also essentially surrounded by spongiosa of relatively low strength. It will be appreciated however that, in the case of long fixing elements, the proximal end of the first portion can also be spread open less wide if it is generally in the region of the stronger corticalis 5.3.

At its periphery the fixing body 1 is provided with tooth-like projections 8 which extend therearound in a ring shape in the non-expanded condition and which, when it is spread open, penetrate into the surrounding bone tissue and provide for additional fixing of the fixing body 1 in the axial direction. It will be appreciated that, in other variants of the invention, these projections may also be of a different configuration and arrangement. In order to perform their purpose, they only have to be designed in such a way that they penetrate into the surrounding bone tissue and then form therewith a positively locking connection in the axial direction of the fixing body. It will be further appreciated that those projections may also be entirely omitted in other variants of the invention. In those variants, the connection between the bone and the fixing element is then made by the positively locking engagement with the bone which, with a spreading effect to varying degrees, is achieved at one or both ends and the middle of the fixing element, and/or the force-locking engagement between the bone and the fixing body.

As can be seen from FIGS. 1 and 2 the fixing body 1 in the illustrated example comprises two body portions 9 and 10 which adjoin each other in the peripheral direction and which are approximately semicylindrical in the non-spread condition (not shown in the Figures). The body portions 9 and 10 are connected together by way of guide projections 12 engaging into guide grooves 11 in the respective other body portion 9 and 10 respectively, for undisturbed spreading of the fixing body 1 In the radial direction. In that arrangement the guide projections 12 extend In the peripheral direction and have guide surfaces 13.1, 13.2 which co-operate with corresponding guide surfaces 14.1, 14.2 of the guide grooves 11. In this case, the guide surfaces 13.1 and 14.1 fix the body portions 9 and 10 relative to each other transversely with respect to the direction of the spreading movement while the guide surfaces 13.2 and 14.2 perform the function of fixing the body portions in the longitudinal direction. In that way the fixing body 1 can be Introduced without any problem in the non-expanded condition into the bores 4 and 6 and are then spread open in a defined manner without the body portions 9, 10 being capable of moving relative to each other in the longitudinal direction. It will be appreciated that the fixing action for the body portions 9, 10 has to persist in that case only until unwanted displacement of the body portions 9, 10 relative to each other is in any case prevented by the regions of the body portions 9, 10, which penetrate into the surrounding bone 4.

It will be appreciated however that the fixing body can also be of a different structure in other variants of the fixing element according to the invention. Thus for example it can also be made up of more than two body portions. The body portions may also be connected integrally to each other by way of corresponding webs or legs or the like, in which case the legs may then not excessively impede the spreading action. For that purpose, they can be so designed that, when the spreading movement takes place, they correspondingly stretch or unfold or however also tear apart. It will be appreciated however that the fixing body may also be formed in one piece with corresponding longitudinal slots or the like, which permit the spreading effect thereof. It will further be appreciated that the outside contour of the fixing body does not necessarily have to be cylindrical. It may for example also be of a prism-like configuration of any, for example polygonal area.

As can further be seen from FIG. 2, the spreading body 2 is of a rectangular cross-section co-operating with correspondingly shaped operative surfaces 15 delimiting the cavity 3 in the fixing body 1. It will be appreciated however that, in other alternative configurations, the spreading body may also be of a different cross-section. Thus for example a circular, elliptical or polygonal cross-section is a possibility, which then co-operates with a correspondingly shaped groove forming the cavity, in the respective body portion.

FIG. 3 is a view in section in the longitudinal direction through half of the embodiment illustrated in FIG. 1 in a partially spread condition. As can be seen from FIG. 3 the transverse dimension of the cavity 3 continuously decreases from approximately the center of the fixing body 1 towards the respective ends thereof. The transverse dimension of the spreading body 2 in comparison decreases towards the distal end in two stages 2.1 and 2.2.

In that respect, at its leading distal end the spreading body 2 is of a transverse dimension which, in the non-spread condition, approximately corresponds to the transverse dimension of the operative surface 15.2 defining the cavity 3, at the distal end of the second portion 1.2. In addition the transverse dimension of the cavity 3 increases from the distal end of the second portion 1.2 in the proximal direction to a greater degree per unit of length than the transverse dimension of the second stage 2.2 of the spreading body 2 from the distal end thereof. That provides that spreading of the second portion 1.2 of the fixing body 1 begins from the distal end thereof. That means that, in the spreading operation, in the second portion, the distribution of stresses achieved is as uniform as possible and thus local stress peaks are substantially avoided both in the fixing body and also in the bone.

In addition, at the distal end of the first stage 2.1 the spreading body 2 is of a transverse dimension which in the non-spread condition—as indicated in FIG. 3 by the contour 16 shown in dash-dotted line—approximately corresponds to the transverse dimension of the operative surface 15.1 defining the cavity 3, at the proximal end of the first portion 1.1. Furthermore, the longitudinal spacing between the distal end of the first stage 2.1 and the distal end of the second stage 2.2 is less than the longitudinal spacing between the distal end of the second portion 1.2 and the proximal end of the first portion 1.1. That provides that the first part 17 of the first portion 1.1, which is at the proximal end, is spread open before spreading of the second portion 1.2. In other words, the fixing body 1 is already anchored at its proximal end in the first bone fragment 5.1 before anchoring in the second bone fragment 5.2 occurs.

Due to the irregular spreading effect, the fixing body 1 is reduced in length in its longitudinal direction, as indicated in FIG. 3 by the contour 18 shown in dash-double-dotted line. The reduction in length of the second portion 1.2 as a result of its spreading which begins at the distal end is transmitted to the first bone fragment 5.1 by way of the first part 17 of the first portion, which is already spread open, so that the first bone fragment is pressed against the second bone fragment 5.2 in a manner which is advantageous in terms of healing.

As indicated by the contour 19 in FIGS. 1 and 3, a spacer sleeve of suitable length can be introduced into the bottom of the bore 6 before insertion of the fixing body 1. Upon insertion of the spreading body 2 into the cavity 3, the spacer sleeve prevents displacement of the fixing body 1 in the distal direction, at least until the fixing body 1 is adequately anchored in the surrounding bone 5 as a result of the spreading movement. It will be appreciated that it is also possible to use other aids for that purpose or that such aids are unnecessary if the longitudinal forces which occur up to the moment of anchoring of the fixing body 1 as a result of the spreading movement in the surrounding bone 5 do not exceed those for displacement of the fixing body 1 in the respective spread condition.

At its proximal end the spreading body 2 also has a projection 2.3 which prevents further introduction of the spreading body 2 into the fixing body 1 when a predetermined end position is reached and which thus ensures an accurately defined spreading effect in each situation of use.

FIG. 4 shows a further preferred embodiment of the fixing element according to the Invention, which in terms of its basic structure corresponds to the variant shown in FIG. 1 so that only the differences will be discussed here. One of those differences is that the first portion 1.1' of the fixing body 1' is of a larger transverse dimension than the second portion 1.2' of the fixing body 1'. In a corresponding manner, the diameter of the bore 4' in the first bone fragment 5.1 is correspondingly larger than the diameter of the bore 6' in the second bone fragment 5.2. The step 20 produced in that way in the region of the fracture gap 7 thus serves as an abutment for the fixing body 1 when it is introduced into the bores 4', 6' in the non-spread condition. That ensures in a simple fashion that on the one hand the fixing body 1 is always arranged in the optimum position relative to the fracture gap 7, Irrespective of the thickness of the first bone fragment 5.1, and that on the other hand, no displacement of the fixing body 1' out of that optimum position can occur due to longitudinal forces which take effect upon introducing the spreading element 2'.

In the illustrated embodiment the first portion 1.1' of the fixing body 1' is uniformly spread while the spreading effect in the second portion 1.2' increases towards the distal end. For that purpose, apart from a bevelled distal end, the spreading body 2' is of a substantially constant transverse dimension, the same applies for the cavity 3' of the first portion 1.1' of the fixing body 1' while the transverse dimension of the cavity 3' in the second portion 1.2' in the non-spread condition decreases In the distal direction. It will be appreciated however that, in other alternative configurations of the invention, spreading of the fixing body can also be implemented in first and second portions of different transverse dimensions, similarly to the embodiment of FIG. 1.

FIG. 5 is a view in section in the longitudinal direction through half of a further embodiment of the fixing element according to the invention in the partially spread condition. The structure here basically corresponds to the variant shown in FIG. 1 so that only the differences will be discussed here.

In this variant, the first portion 1.1" is integrally connected to the second portion 1.2" of the fixing body 2" by way of a leg 21 extending in the peripheral direction. In the illustrated condition the distal end of the spreading body 2" which is of circular cross-section over its entire length is just touching the operative surface 15.2" defining the cavity 3", that is to say upon further forward driving movement of the spreading body 2" in the distal direction, spreading of the second portion 1.2" of the fixing body 2" begins. In that case, as already described in detail with reference to FIG. 3, the second stage 2.2" of the spreading body 2" and the operative surface 15.2" of the second portion 1.2" are so matched to each other that spreading of the second portion 1.2" occurs in a first step at the distal end thereof, before in a second step the proximal end of the second portion 1.2" is spread. In the illustrated condition, the first portion 1.1" is already completely spread open by virtue of the short longitudinal spacing between the first stage 2.1" and the second stage 2.2" of the spreading body 2".

In this case, the leg 21 is arranged on the first and second portions 1.1" and 1.2" in such a way that its angle of inclination relative to the longitudinal axis 1.3 of the fixing body increases during the second step, as is indicated by the contour 22 in FIG. 5. That affords a reduction in the longitudinal spacing between the first and second portions 1.1" and 1.2". The reduction in the longitudinal spacing between the first and second portions 1.1" and 1.2" is transmitted to the first and second bone fragments 5.1 and 5.2 respectively by way of the regions of the first and second portions 1.1" and 1.2" respectively which are already connected to the respective bone fragment 5.1, 5.2 by the spreading action when the reduction in longitudinal spacing begins. In that situation the bone fragments 5.1 and 5.2 are pressed against each other if the resulting reduction in the longitudinal spacing between the first and second portions 1.1" and 1.2" is greater than the initial fracture gap 7 and the pressing force results from the corresponding elastic increase in length of the leg 21.

In the illustrated example once again in the non-spread condition the transverse dimension of the first portion 1.1" is greater than the transverse dimension of the second portion 1.2" so that the fixing body 1" can be introduced into the corresponding bores 4" and 6" in a defined fashion as far as the step 20". In that case the distal end face 23 of the first portion 1.1" bears against the second bone fragment 5.2. In order to ensure that, after the second step, the first and second bone fragments 5.1 and 5.2 are also actually pressed against each other and it is not just the distal end face 23 of the first portion 1.1" that is pressed against the second bone fragment 5.2, a spacer element 24 is provided on the first portion 1.1". That spacer element extends in the,axial direction at a spacing relative to the longitudinal axis 1.3, which is beyond the diameter of the bore 6" in the second bone fragment 5.2. In that respect, the spacer element 24 is such that it can easily penetrate into the second bone fragment 5.2 during the second step. That ensures that after the second step the first and second bone fragments 5.1 and 5.2 are actually also pressed against each other.

The illustrated example has only one spacer element 24 but It will be appreciated that In other variants of the invention, it is also possible to provide a plurality of spacer elements which are distributed around the periphery, or a spacer element which is in the form of a peripherally extending leg, in order to ensure that the indicated effect is achieved in particular when dealing with fractures which extend inclinedly with respect to the bore axis.

The fixing elements shown in FIGS. 1, 4 and 5 in all the components thereof respectively consist of a bioresorbable material so that subsequent explantation thereof is unnecessary. In that respect, the fixing body comprises a polylactide. In the variant shown in FIG. 5 the material in the region of the leg 21 is reinforced by a tension-resistant, bioresorbable fiber cloth. Bioresorbable polyglactide is used in this case, which is also employed for surgical suture materials.

What is claimed is:

1. An element for fixing a first bone fragment, in particular a bone fragment in an ankle joint fracture, to an associated second bone fragment, said fixing element comprising:

an elongate spreading body and an elongate fixing body which can be introduced into aligned bores in the bone fragments and which has a proximal first portion which is to be introduced into the first bone fragment, a distal second portion which adjoins the first portion and which is to be introduced into the second bone fragment, and a cavity which extends substantially over its length, wherein the fixing body is adapted to be introduced completely into the bores, it can be spread open transversely with respect to its longitudinal direction by a wedge action at least at its two ends in longitudinal direction for connection to the respective bone fragment by proximal introduction of the spreading body into the cavity and after substantially complete introduction of the spreading body into the cavity it is of a greater dimension transversely with respect to its longitudinal direction at a distal end of the second potion than at a proximal end of the second portion, characterised in that the fixing body is adapted to be spread open over its entire length.

2. The fixing element as set forth in claim 1 characterised in that the fixing body comprises at least two body portions which adjoin each other in the peripheral direction and which are connected together movably sufficiently for spreading open.

3. The fixing element claim 1 wherein the operative surfaces of the fixing body and the spreading body, which co-operate for spreading open the fixing body, are of such a configuration that spreading of the second portion begins at the distal end of the second portion.

4. The fixing element as set forth in claim 3 characterised in that the co-operating operative surfaces of the fixing body and the spreading body are of such a configuration that at least one first part of the first portion is spread open before the second portion is spread open.

5. The fixing element as set forth in claim 4 characterised in that the first part is arranged in the region of the proximal end of the first portion.

6. The fixing element of claim 5 wherein the first portion is pivotably connected at its distal end by way of at least one leg element to the proximal end of the second portion, wherein the fixing body and the spreading body are of such a configuration that, upon introduction of the spreading body, the distal end of the first portion is substantially completely spread open before in succession in a first step a part of the second portion is spread open and in a second stop the proximal end of the second portion is spread open, or that upon introduction of the spreading body the proximal end of the second portion is substantially completely spread open before in succession in a first step a part of the first portion is spread open and in a second step the distal end of the first portion is spread open, and the leg element is of such a configuration and arrangement that the longitudinal spacing between the first and second portions is reduced during the second step.

7. The fixing element of claim 6 wherein after the spreading body is introduced into the cavity, the fixing body is of a larger dimension transversely with respect to its longitudinal direction at the proximal end of the first portion than at the distal end of the first portion.

8. The fixing element of claim 7 wherein in the non-spread condition the first portion is of a greater dimension transversely with respect to its longitudinal direction than the second portion.

9. The fixing element of claim 8 wherein projections intended to penetrate into the bone are provided at the surface of the fixing body which is towards the bone.

10. The fixing element of claim 9 wherein at least the fixing body comprises a bioresorbable material.

11. The fixing element as set forth in claim 10 wherein the fixing body comprises a polylactide which is reinforced in regions involving a tensile loading by tension-resistant, in particular bioresorbable, fibers and/or fiber cloth.

12. The fixing element of claim 2 wherein the operative surfaces of the fixing body and the spreading body, which co-operate for spreading open the fixing body, are of such a configuration that spreading of the second portion begins at the distal end of the second portion.

13. The fixing element as set forth in claim 12 wherein the co-operating operative surfaces of the fixing body and the spreading body are of such a configuration that at least one first part of the first portion is spread open before the second portion is spread open.

14. The fixing element of claim 13 wherein the first part is arranged in the region of the proximal end of the first portion.

15. The fixing element of claim 14 wherein the first part is pivotably connected at its distal end by way of at least one leg element to the proximal end of the second portion, wherein the first body and the spreading body are of such a configuration that, upon introduction of the spreading body, the distal end of the first portion is substantially completely spread open before in succession in a first step a part of the second portion is spread open and in a second step the proximal end of the second portion is spread open, or that upon introduction of the spreading body the proximal end of the second portion is substantially completely spread open before in succession in a first step a part of the first portion is spread open and in a second stop the distal end of the first portion is spread open, and the leg element is of such a configuration and arrangement that the longitudinal spacing between the first and second portions is reduced during the second step.

16. The fixing element of claim 15 wherein after the spreading body is introduced into the cavity, the fixing body is of a larger dimension transversely with respect to its longitudinal direction at the proximal end of the first portion than at the distal end of the first portion.

17. The fixing element of claim 16 wherein in the non-spread condition the first portion is of a greater dimension transversely with respect to its longitudinal direction than the second portion.

18. The fixing element of claim 17 wherein projections intended to penetrate into the bone are provided at the surface of the fixing body which is towards the bone.

19. The fixing element of claim 18 wherein the fixing body comprises a bioresorbable material.

20. The fixing element of claim 1 wherein the fixing body comprises a bioresorbable material.

21. The fixing element as set forth in claim 19 wherein the fixing body comprises a polylactide which is reinforced in regions involving a tensile loading by tension-resistant, in particular bioresorbable, fibers and/or fiber cloth.

22. The fixing element as set forth in claim 20 wherein the fixing body comprises a polylactide which is reinforced in regions involving a tensile loading by tension-resistant, in particular bioresorbable, fibers and/or fiber cloth.

23. An element for fixing a first bone fragment to an associated second bone fragment from a fracture, especially an ankle joint fracture, each bone fragment having an aligned bore therein, the fixing element comprising:

an elongate fixing body, sized to be introduced into the aligned bores such that a first portion defining a proximal end thereof is introduced into the first bone fragment and a second portion defining a distal end thereof is introduced into the second bone fragment, a proximal end of the second portion adjoining a distal end of the first portion, and the fixing body having an operative surface defined by a cavity extending substantially longitudinally therethrough; and an elongate spreading body for longitudinal introduction into the cavity at the proximal end, an operative surface of the spreading body defined by an external surface thereof, the fixing body operative surface and the spreading body operative surface co-acting to spread open the fixing body transversely with respect to the longitudinal direction thereof by a wedge action for connection to the respective bone fragments, such that after substantially complete introduction of the spreading body into the cavity, the second portion of the fixing body has a greater dimension transversely with respect to the longitudinal direction thereof at the distal end of the second portion than at the proximal end thereof, the fixing body being adapted to be spread open over its entire length.

* * * * *